United States Patent
Brown, III

[11] Patent Number: 6,123,681
[45] Date of Patent: Sep. 26, 2000

[54] ANTI-EMBOLISM STOCKING DEVICE

[75] Inventor: Charles L. Brown, III, Atlanta, Ga.

[73] Assignee: Global Vascular Concepts, Inc., Atlanta, Ga.

[21] Appl. No.: 09/282,647

[22] Filed: Mar. 31, 1999

Related U.S. Application Data

[60] Provisional application No. 60/080,079, Mar. 31, 1998.

[51] Int. Cl.[7] .............................. A61L 15/00; A61H 7/00; A61F 13/00; A41B 11/00
[52] U.S. Cl. .................................. 602/75; 602/62; 602/63; 601/152; 2/239
[58] Field of Search ................................... 623/3; 600/16, 600/490, 499; 607/3, 48, 49, 149, 152; 606/201, 202, 203; 128/DIG. 20; 601/149, 150, 151, 15, 18, 20, 21, 84, 152; 2/239, 240, 409, 242; 223/112

[56] References Cited

U.S. PATENT DOCUMENTS

| | | |
|---|---|---|
| 3,826,249 | 7/1974 | Lee et al. . |
| 4,013,069 | 3/1977 | Hasty . |
| 4,027,667 | 6/1977 | Swallow et al. . |
| 4,030,488 | 6/1977 | Hasty . |
| 4,054,129 | 10/1977 | Byars et al. . |
| 4,091,804 | 5/1978 | Hasty . |
| 4,153,050 | 5/1979 | Bishop et al. . |
| 4,156,425 | 5/1979 | Arkans . |
| 4,172,456 | 10/1979 | Zens ........................................... 602/63 |
| 4,180,065 | 12/1979 | Bowen ................................... 2/239 X |
| 4,198,834 | 4/1980 | Reid, Sr. ................................... 66/172 |
| 4,198,961 | 4/1980 | Arkans . |
| 4,202,325 | 5/1980 | Villari et al. . |
| 4,207,875 | 6/1980 | Arkans . |
| 4,207,876 | 6/1980 | Annis . |
| 4,253,449 | 3/1981 | Arkans et al. . |
| 4,320,746 | 3/1982 | Arkans et al. . |
| 4,375,217 | 3/1983 | Arkans . |
| 4,402,312 | 9/1983 | Villari et al. . |
| 4,513,740 | 4/1985 | Westlake . |
| 4,745,917 | 5/1988 | Hasty et al. . |
| 5,014,681 | 5/1991 | Neeman et al. . |
| 5,022,387 | 6/1991 | Hasty . |
| 5,031,604 | 7/1991 | Dye . |
| 5,179,941 | 1/1993 | Siemssen et al. . |
| 5,186,163 | 2/1993 | Dye . |
| 5,412,957 | 5/1995 | Bradberry et al. ......................... 602/63 |
| 5,540,735 | 7/1996 | Wingrove . |
| 5,814,003 | 9/1998 | Knox et al. ............................... 602/63 |

FOREIGN PATENT DOCUMENTS

| | | |
|---|---|---|
| 542383 | 5/1993 | European Pat. Off. ................. 600/16 |
| 63-236496 | 9/1988 | Japan . |
| 03297089 | 11/1991 | Japan . |
| 92006738 | 4/1992 | WIPO ...................................... 600/16 |

OTHER PUBLICATIONS

Stinson, Stephen, "Plastic gels uses extend to "muscles," valves", Chemical and Engineering News, vol. 68, No. 2, pp. 30–31 (1990).

Shiga, Tohru, "Deformation and Viscoelectric Behavior of Polymer Gels in Electric Fields", Advances in Polymer Science, vol. 134, pp. 131–163 (1997).

Ibaraki University, New Mat./Jap., p. 11, (1991) (abstract only).

*Primary Examiner*—Kim M. Lee
*Attorney, Agent, or Firm*—Jones & Askew, LLP

[57] ABSTRACT

An anti-embolism stocking used to inhibit the development of thrombophlebitis. The present invention is directed to a system and method for applying compressive forces to parts of the body to stimulate fluid flow through the parts of the body. In particular the present invention relates to a stocking that is capable of being placed on a portion of the body and then having a stimulus applied thereto to stimulate blood flow within the region of the body upon which the stocking is placed. The stocking includes polymer materials which, when a selected stimulus is applied thereto, causes constriction of the polymer, thereby causing the compressive forces. The stocking may be designed such that the compressive forces may be generated sequentially along the length of the stocking to gradually stimulate fluid flow, such as blood, to and from the preselected body portion.

25 Claims, 1 Drawing Sheet

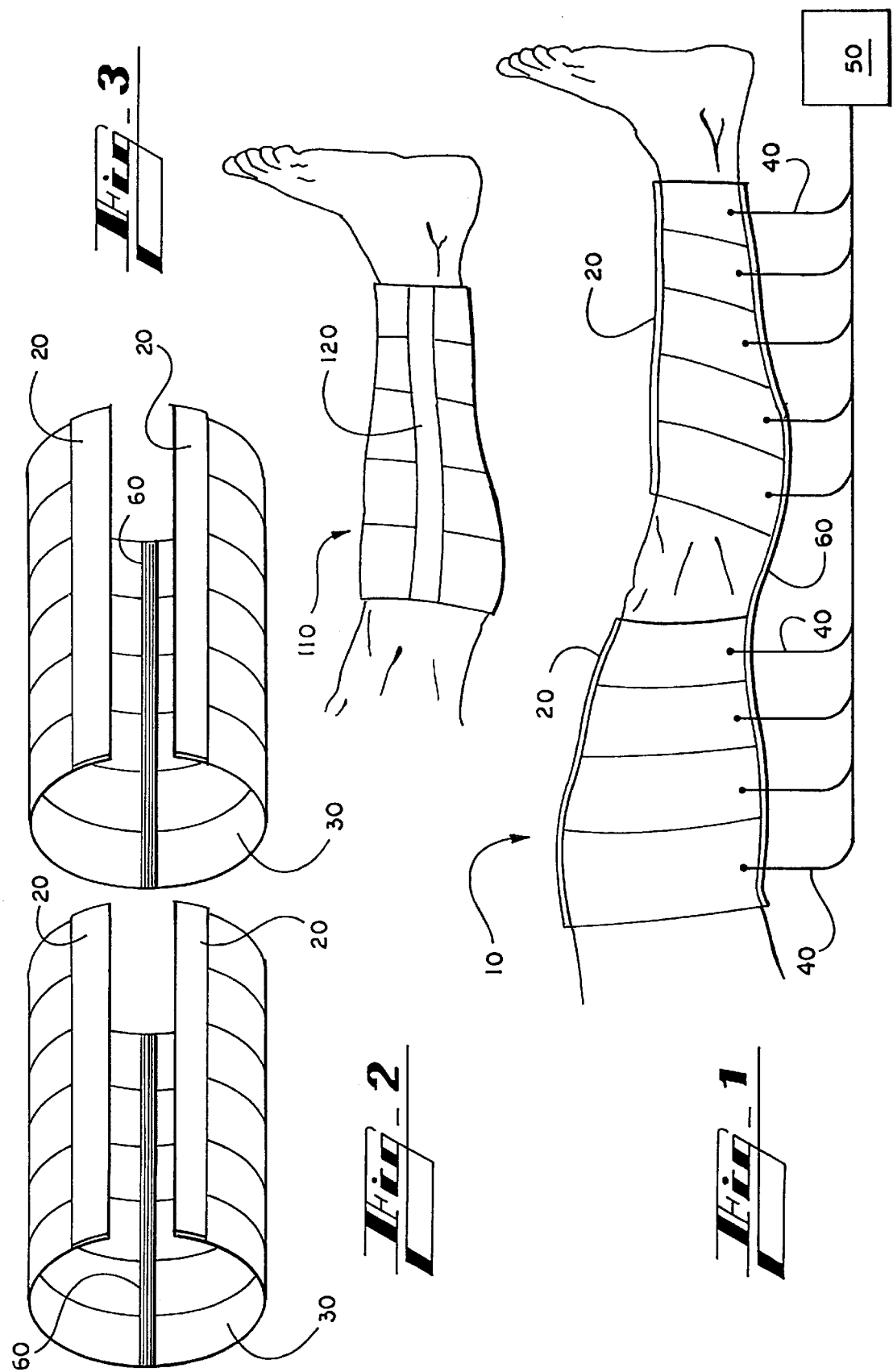

ANTI-EMBOLISM STOCKING DEVICE

CROSS-REFERENCE TO RELATED APPLICATION

This application claims priority to U.S. Provisional Patent Application Ser. No. 60/080,079, filed Mar. 31, 1998.

FIELD OF THE INVENTION

The present invention relates generally to a system and method for applying compressive forces to parts of the body to stimulate blood flow. In particular the present invention relates to a stocking that is capable of being placed on a portion of the body and then having a stimulus applied thereto to stimulate blood flow within the region of the body upon which the stocking is placed.

BACKGROUND OF THE INVENTION

Various compressive devices for a multitude of medical uses have been present for many years. The benefit is indicated for several medical problems. The most common, and most threatening, is in the prevention of pulmonary embolism from deep vein thrombosis of the great veins of the legs. Compressive devices have been used for treatment of both venous insufficiency in upper and lower extremities and for the treatment of lymphedema in a limb whose lymph drainage channels have been interrupted by surgery or radiation.

A constant danger to an immobilized patient is the tendency to develop thrombophlebitis with formation of intravascular thrombi which may detach and flow towards the heart and lungs resulting in a pulmonary embolus which may prove fatal. With immobility, the flow of blood in the venous side of the circulatory system is reduced to a point favoring venous stasis and subsequent localized clot formation. Proximal to the adherent clot, the blood in the vein is less adherent to the vessel wall. It is usually this portion of the clot which detaches itself and acts as an embolus to the heart and lungs.

There are many situations in a hospital population where the above pertains, such as the patient who has recently suffered a heart attack, the patient in coma, the patient with a fracture, the post-operative patient who cannot be ambulated, and the burn patient. A potential danger is also during prolonged surgical procedures with the patient completely anesthetized. At present, the only methods to prevent thrombophlebitis with resultant thrombus formation are early ambulation, application of elastic hose and anticoagulant therapy (heparin, coumadin, warfarin sodium, and phenindione). Early ambulation is contraindicated in such patients who have suffered an acute myocardial infarction or fractured hip. Anticoagulants may produce bleeding especially in an early post-operative patient. The elastic hose merely constricts the musculature of the lower extremity but does not mimic the pulsatile milking action of leg muscles upon the veins which enhance venous blood flow back to the heart. It has been the practice in extreme cases, in order to increase blood supply to a local area blocked by an obstruction, to surgically remove the lesion from the artery. When there is severely diminished blood flow through the extremity, ulceration or gangrene may develop and lead to amputation.

In those cases where it is not feasible to administer anticoagulant treatment and surgery is not required, other therapy has been pursued for the purpose of increasing blood circulation through the lower extremities. In the treatment of middle-aged and elderly bedfast patients, it is a well known practice to increase the rate of blood circulation through the lower extremities by constricting the extremities through the use of elastic stockings to prevent thrombus formation. Correctly applied elastic bandages may be used in place of elastic stockings by removing and re-applying them every eight hours, checking the legs for redness, swelling and tenderness.

When there has been destruction of the valves of the deep veins within the lower extremity, a pneumatic legging may be prescribed. The legging is zippered on the patient's leg and has a cloth cover and a rubber bladder inside into which air is pumped to a pressure of 30 mm. Hg. A rhythmic increase in pressure in the veins results as the patient walks. The device is intended for use in cases where the person is fully ambulatory and edema or swelling of the lower extremities is to be prevented. If the patient is unable to walk and is immobilized, no increase in pressure in the veins will occur as the extremity muscles are not stimulated. There is need for a pressure control device to be fitted on the extremity of an immobilized patient to aid in the venous return of blood to the heart for the prevention of thrombus formation.

Additionally, there are devices currently being studied for treatment of angina pectoris by external venous compression, which is performed in sequential sessions over a period of weeks and months.

The devices in use now are crude systems which utilize external compression by either pneumatic or fluid compressive devices wrapped around the limbs. They are all encumbered by the need to attach these to a central console which provides the force of compression through tubes connected to the compression devices. These consoles are normally bulky, frequently noisy and commit the patient to bed rest while in use.

Accordingly, there is need to provide a sequential application of compressive forces for squeezing or constricting the muscles thereof to prevent stasis of blood with resultant thrombus formation in the leg veins and pulmonary emboli associated therewith. Additionally, what is needed are devices for applying compressive forces which are easy to place around the portion of the body which may be subject to thrombophlebitis or venous thrombosis. These devices should also be able to selectively apply the compressive force to allow the device to stimulate fluid flow to and from the portion of the body to be treated.

SUMMARY OF THE INVENTION

The present invention is directed to anti-embolism stocking devices for preventing thrombophlebitis or venous thrombosis by applying pressure to the body to stimulate blood flow. Additionally, the present invention is directed to methods for preventing thrombophlebitis or venous thrombosis by using the anti-embolism stocking of the present invention.

In particular, the present invention relates to a stocking that is constructed and arranged to be placed over a portion of the body. The stocking may be a seamless stocking that is pulled over the body like a sock, or it may be wrapped around the portion of the body and secured using securing means. Additionally, the stocking includes a plurality of polymer strips which are arranged in a preselected pattern on the stocking. The strips may be placed circumferentially along the stocking, or they may be placed longitudinally along the length of the stocking. The polymer strips are made from a material that, upon contact with a stimulus, constrict and cause compression upon the part of the body contacted by the anti-embolism stocking device.

Additionally, the present invention relates to a method of preventing thrombophlebitis or venous thrombosis by placing the anti-embolism stocking of the present invention on the part of the body to be treated and applying a stimulus to constrict the polymer materials. While the type of stimulus applied will vary depending on the type of material, preferably the polymer is one that reacts to an electrical stimulus. Therefore, the anti-embolism stocking of the present invention also preferably includes wires for supplying an electrical stimulus to the polymer strips.

The anti-embolism stocking of the present invention may also comprise polymer strips which are segmented. By using segmented strips, the electrical stimulus may be applied to only a portion of the segments at one time. Then, by applying the stimulus sequentially, the anti-embolism stocking may be used to stimulate fluid flow through the portion of the body to be treated.

Accordingly, it is an object of the present invention to provide an anti-embolism stocking that is capable of being placed on a portion of the body.

It is another object of the present invention to provide an anti-embolism stocking that is seamless and capable of being placed on the body like a sock.

It is still another object of the present invention to provide an anti-embolism stocking that includes polymer strips which constrict when contacted with a stimulus.

It is still another object of the present invention to provide an anti-embolism stocking that includes polymer strips which are segmented to allow for compressive force to be applied in a sequential basis.

It is still another object of the present invention to provide a method for preventing thrombophlebitis or venous thrombosis by placing the anti-embolism stocking of the present invention on the part of the body to be treated and applying a stimulus to constrict the polymer materials.

These and other objects, features and advantages of the present invention will become apparent after a review of the following detailed description of the disclosed embodiments and the appended claims.

BRIEF DESCRIPTION OF THE DRAWINGS

FIG. 1 depicts an anti-embolism stocking of the present invention as oriented on a leg and having a circumferential spacing for the polymer strips.

FIG. 2 depicts an anti-embolism stocking of the present invention having a circumferential spacing for the polymer strips and including means for securing the stocking.

FIG. 3 depicts an anti-embolism stocking of the present invention comprising a seamless stocking and including polymer strips arranged longitudinally along the stocking.

DETAILED DESCRIPTION

The present invention is directed to an anti-embolism stocking device designed to provide compressive benefit by utilizing compressive forces captured by incorporating polymer strips into a wrap-around stocking device. The stocking is used to prevent embolisms caused by thrombophlebitis or venous thrombosis.

The polymer strips used in the present invention are designed to react to a stimulus and constrict or contract, thereby causing the stocking to compress against the part of the body wrapped by the stocking. Additionally, the stocking can be constructed and arranged to apply compressive forces to only a portion of the stocking at a time, thereby stimulating fluid flow, such as blood, in the portion of the body covered by the stocking. Therefore, the stocking can, for example push blood from the lower part of a leg up to the top of the leg and then can push other blood back down.

The present invention may also be used in a method for preventing embolisms caused by thrombophlebitis or venous thrombosis by using the anti-embolism stocking device of the present invention and applying the necessary stimulus to generate the compressive forces.

The stocking may be designed as either a wrap-around device, or it may comprise a stocking which can be pulled on like a sock. The wrap-around stocking provides greater versatility and may be used on many different portions of the body including the arms, legs and/or torso of an individual. The seamless stocking is simpler in construction and, in some instances, is easier to pull onto the desired portion of the body.

The wrap-around version of the stocking preferably includes means for fastening or securing the stocking. These fastening means may include belts, straps, hook-and-loop fasteners, buttons, snaps or other known connecting means. However, the preferred fastening means comprises a hook-and-loop fastener, such as a VELCRO® strip.

The polymers utilized in the present invention are those capable of contracting in response to a stimulus. The stimulus may be an electrical charge, a chemical reaction, a change in temperature, a change in moisture, or any other stimuli which may be used to contract a polymer. However, the stimulus is preferably an electrical charge. Using an electrical charge provides flexibility by permitting the stimulus to be activated or deactivated as desired in a relatively timely manner. Polymers useful in the present invention include, but are not limited to, crosslinked polyacrylamide gels; polyvinyl alcohol/polyacrylic acid (PVA/PAA) gels; polyacrylamide gels; poly(sodium acrylate) gels; poly(2-acrylamide-2-methylpropane)sulfonic gels; polymethacrylic acid and $Ca^{2+}$ gels; poly(3-alkyl-thiophene gels; silicone gels with poly-methacrylic acid cobalt(II) salt particles; silicone gels with lightly doped poly-p-phenylene particles; and crosslinked PVA hydrogels with $Fe_3O_4$ particles.

Referring now to the Figures, FIG. 1 depicts one embodiment comprising an anti-embolism stocking 10 that can be wrapped around any desired body part and secured with a fastening means 20, such as a VELCRO® strip. The stocking 10 includes polymer strips 30 which are arranged around the stocking 10. In this embodiment, the polymer strips 30 are arranged into segments circumferentially around the patient's limb. These segments allow for separate, segmental compression of a section of the limb, to be discussed in greater detail hereafter.

In this embodiment, the stocking 10 also comprises means for receiving an electrical stimulus such as a plurality of wires 40. The wires 40 are individually placed into each polymer strip 30 and connected to a power source 50, such as a battery pack. Alternatively, the power source may be a standard AC wall outlet. This power source 50 generates the electrical energy required to cause shortening of these polymer strip segments, which impacts compressive force to the limb in a circumferential fashion. The power source 50 can be programmed in a variety of ways, such as to send impulses to the most distal segment first, then as this cycle of compression is waning, start compression of the next, more proximal segment. This occurs until the sequence has completed at the most proximal segment. The cycle can then start over again at the most distal segment.

The stocking also includes a support 60 for the stocking 10. The support 60 preferably comprises a fiber or cord which binds the individual stocking segments together.

FIG. 2 shows the stocking 10 of FIG. 1 in an open position and more closely depicts the polymer strip 20 segments and fastening means 30.

The polymer strips 20 shown in FIGS. 1 and 2 are preferably about 3–4 inches in width and are preferably spaced about 2–3 inches from each other. However, the width and spacing of the strips may vary as needed. Additionally, in some embodiments, the polymer strips 20 may be arranged adjacent to one another to eliminate any areas on the limb which are not capable of being treated with compressive force.

Alternatively, as shown in FIG. 3, the anti-embolism stocking 110 may comprise a stocking having no fastening means. The stocking is capable of being pulled onto a limb, such as an arm or leg, by pulling the device on like a sock. Also in FIG. 3, the polymer strips 120 are arranged longitudinally along the stocking 110. However, it is to be appreciated that for any of the embodiments, the polymer strips may be arranged circumferentially, longitudinally, or at a bias, depending on the treatment protocol desired.

Alternatively, while the preceding embodiments disclosed a stocking having polymer strips incorporated into the stocking, it is conceivable that the present invention may be carried out wherein the polymer is located within a series of pouches strategically located around the stocking. When the stimulus is applied, the polymer would change shape, thereby causing constriction of the stocking.

The stocking is preferably made from a material capable of being integrated with the polymer strips. The polymer strips may either be attached directly to the stocking, may be inserted into pre-stitched pockets, or may be interwoven with the stocking material. Preferably, the stocking material comprises an elastomeric material, such as nylon or SPANDEX®, which more closely conforms to the portion of the body treated, thereby helping to ensure that the compressive forces are distributed equally around the portion of the body.

The size of the stocking may vary as needed depending upon the size of the portion of the body to be treated. However, smaller versions of the stocking may be used which allow a patient to ambulate.

The anti-embolism stocking of the present invention may be used in methods to prevent thrombophlebitis or venous thrombosis. In these methods, the stocking is pulled onto or wrapped around and fastened onto the portion of the body to be treated. Then, a stimulus is applied to the polymer strips causing the polymer strips to constrict or contract, thereby causing compressive forces to be applied to the portion of the body. These compressive forces push fluids from the wrapped portion of the body, and therefore, reduce the risk of thrombophlebitis or venous thrombosis in an immobilized patient.

As previously mentioned, the method may include the selective activation of only a portion of the polymer strips. The stimulus would be sent to the most distal segment first to start the initial compression. Then as this cycle of compression is waning, compression of the next, more proximal segment would be started. This progression would occur until the sequence has completed at the most proximal segment. The cycle can then start over again at the most distal segment. This sequential treatment protocol may be used to stimulate fluid flow by pushing stagnant fluids from the body portion and then drawing fresher fluids into the body portion. An automatic control means may be used to operate this sequential treatment at its optimum efficiency.

Other uses of the invention include long term ambulatory benefits in patients with chronic venous insufficiency or for long term usage in patients with chronic lymphedema. Depending upon the compressive forces generated, the invention can also be modified for use as an external compression device for the treatment of angina pectoris.

I claim:

1. An anti-embolism stocking device comprising:
    a stocking capable of being wrapped around a portion of a body;
    a plurality of segmented polymer strips arranged in a preselected orientation along the stocking; and
    means for receiving an electrical stimulus such that when the stimulus is applied to each of the polymer strips in a sequential order, the polymer strips constrict, thereby causing separate, segmental compression to be exerted upon the portion of the body.

2. The stocking device of claim 1, further comprising fastening means for securing the stocking around the portion of the body.

3. The stocking device of claim 2, wherein the fastening means are selected from straps, belts, buttons, snaps, or hook-and-loop fasteners.

4. The stocking device of claim 1, wherein the stocking comprises a tubular stocking which is capable of being placed on a limb of a body.

5. The stocking of claim 1, wherein the means for receiving comprises a plurality of wires connected to each of the polymer strips respectively and also connected to an electrical power source to provide an electrical stimulus individually to the polymer strips to cause the polymer strips to constrict.

6. The stocking device of claim 1, wherein the polymer strips are arranged circumferentially along the length of the stocking.

7. The stocking device of claim 1, wherein the polymer strips are arranged longitudinally along the length of the stocking.

8. The stocking of claim 1, wherein the stimulus may be applied to the polymer strip segments in a sequential order to stimulated fluid flow through the portion of the body.

9. The stocking device of claim 1, wherein the polymer strips are selected from the group consisting of: crosslinked polyacrylamide gels; polyvinyl alcohol/polyacrylic acid (PVA/PAA) gels; polyacrylamide gels; poly(sodium acrylate) gels; poly(2-acrylamide-2-methylpropane)sulfonic gels; polymethacrylate acid and $Ca^{2+}$ gels; poly(3-alkyl-thiophene gels; silicone gels with poly-methacrylic acid cobalt (II) salt particles; silicone gels with lightly doped poly-p-phenylene particles; and crosslinked PVA hydrogels with $Fe_3O_4$ particles.

10. A system for applying compressive forces to a portion of a body comprising:
    a stocking capable of being wrapped around the portion of a body;
    a plurality of segmented polymer strips arranged in a preselected orientation along the stocking; and
    means for applying an electrical stimulus to each of the polymer strips in a segmental order to cause the strips to constrict thereby causing separate, segmental compression to be exerted upon the portion of the body.

11. The system of claim 10, further comprising fastening means for securing the stocking around the portion of the body.

12. The system of claim 10, wherein the stocking comprises a tubular stocking which is capable of being placed on a limb of a body.

13. The system of claim 10, wherein the means for applying a stimulus comprise a plurality of wires connected to each of the polymer strips respectively and also connected to an electrical power source to provide an electrical stimulus individually to the polymer strips to cause the polymer strips to constrict.

14. The system of claim 10, wherein the polymer strips are arranged circumferentially along the length of the stocking.

15. The system of claim 10, wherein the polymer strips are arranged longitudinally along the length of the stocking.

16. The system of claim 10, wherein the stimulus may be applied to the polymer strip segments in a sequential order to stimulate fluid flow through the portion of the body.

17. The stocking device of claim 10, wherein the polymer strips are selected from the group consisting of: crosslinked polyacrylamide gels; polyvinyl alcohol/polyacrylic acid (PVA/PAA) gels; polyacrylamide gels; poly(sodium acrylate) gels; poly(2-acrylamide-2-methylpropane)sulfonic gels; poly methacrylate acid and $Ca^{2+}$ gels; poly(3-alkyl-thiophene gels; silicone gels with poly-methacrylic acid cobalt (II) salt particles; silicone gels with lightly doped poly-p-phenylene particles; and crosslinked PVA hydrogels with $Fe_3O_4$ particles.

18. A method for applying compressive forces to a portion of a body, comprising the steps of:
   surrounding the portion of the body with an anti-embolism stocking; and
   applying an electrical stimulus to the stocking to cause the stocking to apply the compressive force to the portion of the body;
   wherein the anti-embolism stocking comprises:
      a stocking capable of being wrapped around the portion of a body;
      a plurality of segmented polymer strips arranged in a preselected orientation along the stocking; and
      means for applying a stimulus to each of the polymer strips in a sequential order to cause the strips to constrict thereby causing separate, segmental compressing to be extended upon the portion of the body.

19. The method of claim 18, further comprising fastening means for securing the stocking around the portion of the body.

20. The method of claim 19, wherein the stocking comprises a tubular stocking which is capable of being placed on a limb of a body.

21. The method of claim 19, wherein the electrical stimulus is applied to each of the polymer strips individually using a plurality of wires connected to each the polymer strips individually using a plurality of wires connected to each of the polymer strips respectively and also connected to an electrical power source to provide electrical stimulus individually to the polymer strips to cause the polymer strips to constrict.

22. The method of claim 19, wherein the polymer strips are arranged circumferentially along the length of the stocking.

23. The method of claim 19, wherein the polymer strips are arranged longitudinally along the length of the stocking.

24. The method of claim 19, wherein the polymer strips stimulate fluid flow through the portion of the body.

25. The method of claim 19, wherein the polymer strips are selected from the group consisting of: crosslinked polyacrylamide gels; polyvinyl alcohol/polyacrylic acid (PVA/PAA) gels; polyacrylamide gels; poly(sodium acrylate) gels; poly(2-acrylamide-2-methylpropane)sulfonic gels; poly methacrylate acid and $Ca^{2+}$ gels; poly(3-alkyl-thiophene gels; silicone gels with poly-methacrylic acid cobalt (II) salt particles; silicone gels with lightly doped poly-p-phenylene particles; and crosslinked PVA hydrogels with $Fe_3O_4$ particles.

* * * * *